US006544732B1

(12) United States Patent
Chee et al.

(10) Patent No.: US 6,544,732 B1
(45) Date of Patent: Apr. 8, 2003

(54) ENCODING AND DECODING OF ARRAY SENSORS UTILIZING NANOCRYSTALS

(75) Inventors: Mark S. Chee, Del Mar, CA (US); Steven M. Barnard, San Diego, CA (US); Chanfeng Zhao, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 09/315,584

(22) Filed: May 20, 1999

(51) Int. Cl.$^7$ ............................................. G01N 31/00
(52) U.S. Cl. ..................... 435/6; 436/2; 436/4; 436/5; 436/518; 436/523; 436/524; 436/164; 436/805; 436/823; 435/7.1; 435/174
(58) Field of Search ................................ 436/8, 2, 4, 5, 436/518, 523, 524, 164, 805, 823; 435/7.1, 174

(56) References Cited

U.S. PATENT DOCUMENTS

| | | | |
|---|---|---|---|
| 4,200,110 A | | 4/1980 | Peterson |
| 4,224,198 A | * | 9/1980 | Rembaum et al. .............. 260/8 |
| 4,499,052 A | | 2/1985 | Fulwyler |
| 4,682,895 A | | 7/1987 | Costello |
| 4,785,814 A | | 11/1988 | Kane |
| 4,822,746 A | | 4/1989 | Walt |
| 4,824,789 A | | 4/1989 | Yafuso et al. |
| 4,999,306 A | | 3/1991 | Yafuso et al. |
| 5,002,867 A | | 3/1991 | Macevicz |
| 5,026,599 A | * | 6/1991 | Koskenmaki ............... 428/328 |
| 5,028,545 A | | 7/1991 | Soini |
| 5,105,305 A | | 4/1992 | Betzig et al. |
| 5,114,864 A | | 5/1992 | Walt |
| 5,132,242 A | | 7/1992 | Cheung |
| 5,143,853 A | | 9/1992 | Walt |
| 5,185,178 A | * | 2/1993 | Koshkenmaki ............. 427/585 |
| 5,194,300 A | | 3/1993 | Cheung |
| 5,222,092 A | | 6/1993 | Hench et al. |
| 5,244,636 A | | 9/1993 | Walt et al. |
| 5,244,813 A | | 9/1993 | Walt et al. |
| 5,250,264 A | | 10/1993 | Walt et al. |
| 5,252,494 A | | 10/1993 | Walt |
| 5,254,477 A | | 10/1993 | Walt |
| 5,298,741 A | | 3/1994 | Walt et al. |
| 5,302,509 A | | 4/1994 | Cheeseman |
| 5,320,814 A | | 6/1994 | Walt et al. |
| 5,357,590 A | | 10/1994 | Auracher |
| 5,380,489 A | | 1/1995 | Sutton et al. |
| 5,435,724 A | | 7/1995 | Goodman et al. |
| 5,474,895 A | | 12/1995 | Ishii et al. |
| 5,481,629 A | | 1/1996 | Tabuchi |
| 5,494,798 A | | 2/1996 | Gerdt et al. |
| 5,494,810 A | | 2/1996 | Barany et al. |
| 5,496,997 A | | 3/1996 | Pope |
| 5,505,928 A | | 4/1996 | Alivisatos et al. |
| 5,512,490 A | | 4/1996 | Walt et al. |
| 5,516,635 A | | 5/1996 | Ekins et al. |
| 5,518,883 A | | 5/1996 | Soini |
| 5,537,000 A | | 7/1996 | Alivisatos et al. |
| 5,565,324 A | | 10/1996 | Still et al. |
| 5,573,909 A | | 11/1996 | Singer et al. |
| 5,575,849 A | | 11/1996 | Honda et al. |
| 5,604,097 A | | 2/1997 | Brenner |
| 5,633,972 A | | 5/1997 | Walt et al. |
| 5,639,603 A | | 6/1997 | Dower et al. |
| 5,656,241 A | | 8/1997 | Seifert et al. |
| 5,656,815 A | | 8/1997 | Justus et al. |
| 5,679,524 A | | 10/1997 | Nikivorov et al. |
| 5,690,894 A | | 11/1997 | Pinkel et al. |
| 5,747,180 A | | 5/1998 | Miller et al. |
| 5,751,018 A | * | 5/1998 | Alivisatos et al. ............ 257/64 |
| 5,763,175 A | | 6/1998 | Brenner |
| 5,780,231 A | | 7/1998 | Brenner |
| 5,795,714 A | | 8/1998 | Cantor et al. |
| 5,814,524 A | | 9/1998 | Walt |
| 5,830,711 A | | 11/1998 | Barany et al. |
| 5,840,256 A | | 11/1998 | Demers et al. |
| 5,849,215 A | | 12/1998 | Gin et al. |
| 5,854,684 A | | 12/1998 | Stabile et al. |
| 5,856,083 A | | 1/1999 | Chelsky et al. |
| 5,858,732 A | | 1/1999 | Solomon et al. |
| 5,863,708 A | | 1/1999 | Zanzucchi et al. |
| 5,881,200 A | | 3/1999 | Burt |
| 5,888,723 A | | 3/1999 | Sutton et al. |
| 5,888,885 A | | 3/1999 | Xie |
| 5,900,481 A | | 5/1999 | Lough et al. |
| 5,985,353 A | * | 11/1999 | Lawton et al. ............. 427/2.13 |
| 5,990,479 A | * | 11/1999 | Weiss et al. ................ 250/307 |
| 6,005,707 A | * | 12/1999 | Berggren et al. ........... 359/322 |

(List continued on next page.)

FOREIGN PATENT DOCUMENTS

| | | |
|---|---|---|
| EP | 0 269 764 | 6/1988 |
| EP | 0 392 546 | 10/1990 |
| EP | 0 478 319 | 4/1992 |

(List continued on next page.)

OTHER PUBLICATIONS

Ronaghi et al., "A Sequencing Method Based on Real–Time Pyrophosphate," Science, 281:363–365 (1998).

Shoemaker et al., "Quantitative phenotypic analysis of yeast deletion mutants using a highly parallel moelcular bar–coding strategy," Nature Genetics, 14:450–456 (1996).

Bruchez et al., "Semiconductor Nanocrystals as Fluorescent Biological Labels," Science, 281:2013–2016 (1998).

Czarnik, "Illuminating the SNP Genomic Code," Modern Drug Discovery, 1(2): 49–55 (1998).

(List continued on next page.)

*Primary Examiner*—Christopher L. Chin
*Assistant Examiner*—Pensee Do
(74) *Attorney, Agent, or Firm*—Dorsey & Whitney LLP; Robin M. Silva; David C. Foster

(57) ABSTRACT

Described herein are assays and components for encoding and decoding microspheres. Each assay or component described utilizes at least one nanocrystal.

18 Claims, No Drawings

U.S. PATENT DOCUMENTS

| | | | |
|---|---|---|---|
| 6,013,456 A | | 1/2000 | Akhavan-Tafti |
| 6,013,591 A | * | 1/2000 | Ying et al. .................. 501/1 |
| 6,023,540 A | * | 2/2000 | Walt et al. .................. 385/12 |
| 6,027,889 A | | 2/2000 | Barany et al. |
| 6,039,894 A | * | 3/2000 | Sanjurjo et al. ......... 252/301.4 |
| 6,048,515 A | * | 4/2000 | Kresse et al. .................. 424/9 |
| 6,048,616 A | * | 4/2000 | Gallagher et al. .......... 428/407 |
| 6,051,380 A | | 4/2000 | Sosnowski et al. |
| 6,054,564 A | | 4/2000 | Barany et al. |
| 6,060,743 A | * | 5/2000 | Sugiyama et al. .......... 257/321 |
| 6,083,763 A | | 7/2000 | Balch |
| 6,090,666 A | * | 7/2000 | Ueda et al. .................. 438/257 |
| 6,096,496 A | * | 8/2000 | Frankel ...................... 435/4 |
| 6,100,973 A | * | 8/2000 | Lawandy .................... 356/246 |
| 6,103,868 A | * | 8/2000 | Health et al. ................ 528/482 |
| 6,106,609 A | * | 8/2000 | Yang et al. .................. 117/11 |
| 6,110,678 A | | 8/2000 | Weisburg et al. |
| 6,114,038 A | * | 9/2000 | Castro et al. ................ 428/402 |
| 6,121,075 A | * | 9/2000 | Yamashita .................. 438/149 |
| 6,139,626 A | | 10/2000 | Norris et al. |
| 6,172,218 B1 | | 1/2001 | Brenner |
| 6,207,392 B1 | | 3/2001 | Weiss et al. |
| 6,251,639 B1 | | 6/2001 | Kurn |
| 6,268,148 B1 | | 7/2001 | Barany et al. |
| 6,274,323 B1 | * | 8/2001 | Bruchez et al. .............. 435/6 |
| 6,284,465 B1 | * | 9/2001 | Wolber ........................ 435/6 |

FOREIGN PATENT DOCUMENTS

| | | |
|---|---|---|
| EP | 0 723 146 | 7/1996 |
| WO | 89/11101 | 11/1989 |
| WO | WO 90/09885 A1 | 9/1990 |
| WO | 93/02360 | 2/1993 |
| WO | WO 93/25563 | 12/1993 |
| WO | WO 94/02515 | 2/1994 |
| WO | WO 95/16918 | 6/1995 |
| WO | 96/03212 | 2/1996 |
| WO | 97/14028 | 4/1997 |
| WO | 97/14928 | 4/1997 |
| WO | WO 97/31256 | 8/1997 |
| WO | 97/40385 | 10/1997 |
| WO | WO 97/46704 A1 | 12/1997 |
| WO | WO 98/13523 A1 | 4/1998 |
| WO | WO 98/31836 A1 | 7/1998 |
| WO | 98/40726 | 9/1998 |
| WO | 98/50782 | 11/1998 |
| WO | 98/53093 | 11/1998 |
| WO | 98/53300 | 11/1998 |
| WO | 99/18434 | 4/1999 |
| WO | WO 99/39001 | 8/1999 |
| WO | WO 96/30392 A1 | 10/1999 |
| WO | 99/60170 | 11/1999 |
| WO | WO 99/64867 A1 | 12/1999 |
| WO | 99/67414 | 12/1999 |
| WO | WO 99/67641 A2 | 12/1999 |
| WO | 00/04372 | 1/2000 |
| WO | 00/13004 | 3/2000 |
| WO | 00/16101 | 3/2000 |
| WO | WO 00/39587 A1 | 7/2000 |
| WO | WO 00/47996 A2 | 8/2000 |
| WO | 00/48000 | 9/2000 |
| WO | WO 00/58516 | 10/2000 |
| WO | WO 00/63437 A2 | 10/2000 |
| WO | WO 00/71243 A1 | 11/2000 |
| WO | WO 00/71992 A1 | 11/2000 |
| WO | WO 00/71995 A2 | 11/2000 |
| WO | WO 00/75373 A2 | 12/2000 |

OTHER PUBLICATIONS

Ferguson et al., "A Fiber–Optic DNA Biosensor Microarray for the Analysis of Gene Expression," Nature Biotechnology, 14:1681–1684 (1996).

Healey et al., "Improved Fiber–Optic Chemical Sensor for Penicillin," Anal. Chem. 67(24):4471–4476 (1995).

Healey et al., "Development of a Penicillin Biosensor Using a Single Optical Imaging Fiber," SPIE Proc. 2388:568–573 (1995).

Michael et al., "Making Sensors out of Disarray: Optical Sensor Microarrays," Proc. SPIE, 3270: 34–41 (1998).

Michael et al., "Randomly Ordered Addressable High–Density Optical Sensor Arrays," Anal. Chem. 70(7): 1242–1248 (Apr. 1998).

Michael et al., "Fabrication of Micro– and Nanostructures Using Optical Imaging Fibers and there Use as Chemical Sensors," Proc. 3rd Intl. Symp., Microstructures and Microfabricated Systems, ed. P.J. Hesketh, et al., v. 97–5, Electrochem. Soc., 152–157 (Aug. 1997).

Pantano et al., "Ordered Nanowell Arrays," Chem. Mater., 8(12): 2832–2835 (1996).

Walt, D. "Fiber Optic Imaging Sensors," Accounts of Chemical Research, 31(5): 267–278 (1998).

Walt, "Fiber–Optic Sensors for Continuous Clinical Monitoring," Proc. IEEE, 80(6): 903–911 (1992).

Anonymous, "Fluorescent Microspheres," Tech. Note 19, Bang Laboratories, (Fishers, In) Feb. 1997.

Anonymous, "Microsphere Selection Guide," Bang Laboratories, (Fisher, In) Sep. 1998.

Bangs, L.B., "Immunological Applications of Microspheres," The Latex Course, Bangs Laboratories (Carmel, IN) Apr. 1996.

Peterson, J. et al., "Fiber Optic pH Probe for Physiological Use," Anal. Chem., 52:864–869 (1980).

Pope, E. "Fiber Optic Chemical Microsensors Employing Optically Active Silica Microspehres," SPIE, 2388:245–256 (1995).

Strachan et al., "A Rapid General Method for the Identification of PCR Products Using a Fibre–Optic Biosensor and its Application to the Detection of Listeria," Letters in Applied Microbiology, 21:5–9 (1995).

Abel et al., "Fiber–Optic Evanescent Wave Biosensor for the Detection of Oligonucleotides," Anal. Chem. 68:2905–2912 (1996).

Piunno et al., "Fiber–Optic DNA Sensor for Fluorometric Nucleic Acid Determination," Anal. Chem., 68:2635–2643 (1995).

Drmanac, R. et al., "Sequencing by Oligonucleotide Hybridization: A Promising Framework in Decoding of the Genome Program," The First International Conference on Electrophoresis, Supercomputing and the Human Genome, Proceedings os th Apr. 10–13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

Barnard et al., "A Fibre–Optic Chemical Sensor with Discrete Sensing Sites," Nature, 353:338–340 (Sep. 1991).

Fuh et al., "Single Fibre Optic Fluorescence pH Probe," Analyst, 112:1159–1163 (1987).

Mignani et al., "In–Vivo Biomedical Monitoring by Fiber–Optic Systems," Journal of Lightwave Technology, 13(7):1396–1406 (1995).

Healey et al., "Fiberoptic DNA Sensor Array Capable of Detecting Point Mutations," Analytical Biochemistry, 251:270–279 (1997).

Hirschfeld et al., "Laser–Fiber–Optic 'Optrode' for Real Time In Vivo Blood Carbon Dioxide Level Monitoring," Journal of Lightwave Technology, LT–5(7):1027–1033 (1987).

Peterson et al., "Fiber–Optic Sensors for Biomedical Applications," Science, 13:123–127 (1984).

Milanovich et al., "Clinical measurements using fiber optics and optrodes," *Novel Optical Fiber Techniques for Medical Applications*, SPIE, 494:18–31 (1984).

Seitz et al., "Chemical Sensors Based on Immobilized Indicators and Fiber Optics," *C.R.C. Critical Reviews in Analytical Chemistry*, 19(2):135–173 (1988).

Wolfbeis, "Fiber Optical Fluorosensors in Analytical Chemistry," *Molecular Luminescense Spectroscopy, Methods and Applications* (S.G. Schulman, editor), Wiley & Sons, New York, 129–280 (1988).

Angel, "Optrodes: Chemically Selective Fiber–Optic Sensors," *Spectroscopy*, 2(4):38–47 (1987).

Walt et al., "Design, Preparation, and Applications of Fiber–Optic Chemical Sensors for Continuous Monitoring," *Fiber Optic Chemical Sensors, Chemical Sensors and Microinstrumentation*, 252–272 (1989).

Freeman et al., "Oxygen Probe Based on Tetrakis(alkylamino)ethylene Chemiluminescence," *Anal. Chem.*, 53:98–102 (1981).

Lippitsch et al., "Fiber–Optic Oxygen Sensor with the Fluorescence Decay Time as the Information Carrier," *Anal. Chem. Acta.*, 205:1–6 (1998).

Wolfbeis et al., "Fiber–Optic Fluorosensor for Oxygen and Carbon Dioxide," *Anal. Chem.*, 60:2028–2030 (1998).

Doyle, "High Temperature Sample Holder for Fast–Atom Bombardment Mass Spectrometry of Molten Materials," *Anal. Chem.*, 59:537–539 (1987).

Lubbers et al., "Optical Fluorescense Sensors for Continuous Measurement of Chemical Concentrations in Biological Systems," *Sens. Actuators*, 4:641–654 (1983).

Munkholm et al., "A Fiber–Optic Sensor for $CO_2$ Measurement," *Talanta*, 35(2):109–112 (1988).

Munkholm et al., "Polymer Modification of Fiber Optic Chemical Sensors as a Method of Enhancing Fluorescense Signal for pH Measurement," *Anal. Chem.*, 58:1427–1430 (1986).

Seitz, "Chemical Sensors Based on Fiber Optics," *Anal. Chem.*, 56(1):16A–34A (1984).

Saari et al., "pH Sensor Based on Immobilized Fluoresceinamine," *Anal. Chem.*, 54:821–823 (1982).

Zhujun et al., "A Fluorescence Sensor for Quantifying pH in the Range for 6.5 to 8.5," *Anal. Chem. Acta.*, 160:47–55 (1984).

Schwab et al., "Versatile, Efficient Raman Sampling with Fiber Optics," *Anal. Chem.*, 56:2199–2204 (1984).

Pantano et al., "Analytical Applications of Optical Imaging Fibers," *Anal. Chem.*, 67:481A–487A (1995).

Chan et al., "Quantam Dot Bioconjugates for Ultrasensitive Nonisotopic Detection," *Science*, 281:2016–2018 (1998).

Michael et al., "Randomly Ordered Addressable High–Density Optical Sensor Arrays," *Anal. Chem.*, 70:1242–1248 (1998).

Bawendi et al., "The Quantum Mechanics of Larger Semiconductor Clusters ('Quantum Dots')," *Annu. Rev. Phys. Chem.*, 41:477–496 (1990).

Corriu et al., "Recent Developments of Molecular Chemistry for Sol–Gel Processes," *Agnew. Chem. Int. Ed. Engel.*, 35:1420–1436 (1996).

Chen et al., "A Microsphere–Based Assay for Multiplexed Single Nucleotide Polymorphism Analysis Using Single Base Chain Extension," Genome Research, 10(4):549–557 (2000).

Iannone et al., "Multiplexed Single Nucleotide Polymorphism Genotyping by Oligonucleotide Ligation and Flow Cytometry," Cytometry, 39:131–140 (2000).

Lyamichev et al., "Polymorphism identification and quantitative detection of genomic DNA by invasive cleavage of oligonucleotide probes," Nature Biotechnology, 17:292–296 (1999). (added Apr. 3, 2001 892 68087–2).

* cited by examiner

ENCODING AND DECODING OF ARRAY SENSORS UTILIZING NANOCRYSTALS

FIELD OF THE INVENTION

The invention relates to compositions and methods for encoding, decoding and using microsphere array sensors utilizing nanocrystals (also referred to in the art as quantum dots).

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Of particular use in these sensors are detection mechanisms utilizing luminescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C Critical Reviews In Analytical Chemistry*, Vol. 19, 1988, pp. 135–173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch et al., *Anal. Chem. Acta.* 205:1, (1988); Wolfbeis et al., *Anal. Chem.* 60:2028 (1988); Jordan, et al., *Anal. Chem.* 59:437 (1987); Lubbers et al., *Sens. Actuators* 1983; Munkholm et al., *Talanta* 35:109 (1988); Munkholm et al., *Anal. Chem.* 58:1427 (1986); Seitz, W. R., *Anal. Chem.* 56:16A–34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun et al., *Anal. Chem. Acta.* 160:47 (1984); Schwab, et al., *Anal. Chem.* 56:2199 (1984); Wolfbeis, O. S., "Fiber Optic Chemical Sensors", *Ed. CRC Press*, Boca Raton, Fla., 1991, 2nd Volume; and Pantano, P., Walt, D. R., *Anal. Chem.*, 481A–487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Ser. Nos. 08/818,199 and 09/151,877 describe array compositions that utilize microspheres or beads on a surface of a substrate, for example on a terminal end of a fiber optic bundle, with each individual fiber comprising a bead containing an optical signature. Since the beads go down randomly, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

Unfortunately, the above systems all suffer from the disadvantages of working with conventional detection labels, typically organic dyes such as rhodamine. Conventional dye molecules impose stringent requirements on the optical systems used to make these measurements; their narrow excitation spectrum makes simultaneous excitation difficult in most cases, and their broad emission spectrum with a long tail at red wavelengths introduces spectral cross talk between different detection channels, making quantitation of the relative amounts of different probes difficult.

Therefore, it is desirable to provide assay components and methods which utilize detectable labels which emit spectrally resolvable energies and have narrow, symmetric emission spectrums, and wherein whole groups of detectable labels can be excited at a single wavelength.

SUMMARY OF THE INVENTION

In accordance with the above objects, the present invention provides compositions comprising a substrate with a surface comprising discrete sites, and a population of microspheres distributed on the sites. At least one of the microspheres comprises a nanocrystal. The nanocrystal can be embedded in the microsphere, for example using the sol-gel polymerization process, or it can be attached to the microsphere. The microspheres optionally comprise bioactive agents and/or identifier binding ligands.

In an additional aspect, the population of microspheres comprises at least a first and a second subpopulation comprising a first and a second bioactive agent, respectively, and a first and a second optical signature, respectively, capable of identifying each bioactive agent. At least one of the optical signatures comprises a nanocrystal.

In a further aspect, the invention provides methods of making a composition comprising forming a surface comprising individual sites on a substrate and distributing microspheres on the surface such that the individual sites contain microspheres. The microspheres comprise an optical signature, and at least one optical signature comprises at least one nanocrystal.

In an additional aspect the invention provides a method of determining the presence of a target analyte in a sample comprising contacting the sample with a composition. The composition comprises a substrate with a surface comprising discrete sites and a population of microspheres comprising at least a first and a second subpopulation each comprising a bioactive agent and an optical signature capable of identifying the bioactive agent. The microspheres are distributed on the surface such that the discrete sites contain microspheres and wherein at least one of the optical signatures comprises at least one nanocrystal. The presence or absence of the target analyte is then determined.

In a further aspect, the invention provides methods of making a composition comprising adhering nanocrystals to porous silica, and sealing the pores of the silica using the sol-gel polymerization process.

DETAILED DESCRIPTION OF THE INVENTION

The present invention is an improvement on previous work comprising a bead-based analytic chemistry system in which beads, also termed microspheres, carrying different chemical functionalities are distributed on a substrate comprising a patterned surface of discrete sites that can bind the individual microspheres. The beads are generally put onto the substrate randomly, and thus several different methodologies can be used to "decode" the arrays. In one embodiment, unique optical signatures are incorporated into the beads, generally fluorescent dyes, that can be used to identify the chemical functionality on any particular bead. The present invention provides for the first time, an improvement to the previous work by utilizing nanocrystals (also referred to as "quantum dots" or "semi-conductor clusters") in at least one component of the optical signatures as further outlined below.

In comparison to organic dyes such as rhodamine, nanocrystals are approximately at least 20 times as bright, approximately at least 100 times as stable against photobleaching, and are approximately one-third as wide in the emission spectral linewidth. See, for example, Bruchez, et al., Science, 281:2013–2016 (1998); Chan and Nie, Science, 281:2016–2018 (1998); Bawendi et al., Annu. Rev. Phys. Chem. 41:477–496 (1990), and references cited therein, all of which are expressly incorporated by reference. The brightness, stability and narrowness of emission bandwidth all contribute to the ability to use a relatively large number of different colors as further described below (i.e. different size nanocrystals) while preserving the ability to resolve them from each other, and to resolve different quantities of each nanocrystal. In addition, the broad excitation spectrum allows many different nanocrystals to be excited by a common light source.

The use of microsphere arrays allows the synthesis of the candidate agents (i.e. compounds such as nucleic acids and antibodies) to be divorced from their placement on an array, i.e. the candidate agents may be synthesized on the beads, and then the beads are randomly distributed on a patterned surface. The random placement of the beads on the surface means that the array must be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art. These methods are generally outlined in PCT US98/05025 and U.S. Ser. Nos. 08/818,199 and 09/151,877, all of which are expressly incorporated herein by reference. The use of nanocrystals as described herein improves upon the methods formerly described.

Since the placement of the bioactive agents is generally random, a coding/decoding system is required to identify the bioactive agent at each location in the array. This may be done in a variety of ways, as is more fully outlined below, and generally includes: a) the use of optical signatures, including nanocrystals; b) the use a decoding binding ligand (DBL), generally directly labeled, that binds to either the bioactive agent or to identifier binding ligands (IBLs) attached to the beads; c) positional decoding, for example by either targeting the placement of beads (for example by using photoactivatible or photocleavable moieties to allow the selective addition of beads to particular locations), or by using either sub-bundles or selective loading of the sites, as are more fully outlined below; d) selective decoding, wherein only those beads that bind to a target are decoded; or e) combinations of any of these. In some cases, as is more fully outlined below, decoding may occur for all the beads, or only for those that bind a particular target analyte. Similarly, this may occur either prior to or after addition of a target analyte.

In the preferred embodiment, each assay or component provided utilizes at least one component which comprises at least one nanocrystal. The nanocrystals described herein may be used in two general ways. In a preferred embodiment, nanocrystals are used as all or part of optical signatures of the beads; that is, the beads are "coded" with nanocrystals. Alternatively, the nanocrystals can be used as labels in assays; for example, a target nucleic acid may be labeled with nanocrystals and used to detect the target nucleic acid. Both systems are more fully outlined below.

Once the identity (i.e. the actual agent) and location of each microsphere in the array has been fixed, the array is exposed to samples containing the target analytes, although as outlined below, this can be done prior to or during the analysis as well. The target analytes will bind to the bioactive agents as is more fully outlined below, and results in a change in the optical signal of a particular bead. In another embodiment, also more fully outlined below, the target analyte comprises at least one nanocrystal.

In the present invention, "decoding" can use optical signatures, decoding binding ligands that are added during a decoding step, or a combination of these methods. The decoding binding ligands will bind either to a distinct identifier binding ligand partner that is placed on the beads, or to the bioactive agent itself, for example when the beads comprise single-stranded nucleic acids as the bioactive agents. The decoding binding ligands are either directly or indirectly labeled, and thus decoding occurs by detecting the presence of the label. In the preferred embodiment, the label comprises at least one nanocrystal. By using pools of decoding binding ligands in a sequential fashion, it is possible to greatly minimize the number of required decoding steps.

Accordingly, the present invention provides array compositions comprising at least a first substrate with a surface comprising individual sites. By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, (with all numbers being per square centimeter) with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 $\mu$m or less (with beads of 200 nm possible) can be used, and very small fibers are known, it is possible to have as many as 250,000 or more (in some instances, 1 million) different fibers and beads in a 1 mm$^2$ fiber optic bundle, with densities of greater than 15,000,000 individual beads and fibers (again, in some instances as many as 25–50 million) per 0.5 cm$^2$ obtainable.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

At least one surface of the substrate is modified to contain discrete, individual sites for later association of microspheres (or, when microspheres are not used, for the attachment of the bioactive agents). These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate. When the first substrate comprises both the assay locations and the individual arrays, a preferred method utilizes molding techniques that form the bead wells in the bottom of the assay wells in a microtiter plate.

In a preferred embodiment, physical alterations are made in a surface of the substrate to produce the sites. In a preferred embodiment, for example when the second substrate is a fiber optic bundle, the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either bioactive agent attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending the on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached (either covalently or non-covalently) to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by.reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155–200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155–200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems*, 7(4):275–308 (1991), expressly incorporated herein). Proteinaceous candidate agents may also be attached using other techniques known in the art, for example for the attachment of antibodies to polymers; see Slinkin et al., *Bioconj. Chem.* 2:342–348 (1991); Torchilin et al., supra; Trubetskoy et al., *Bioconj. Chem.* 3:323–327 (1992); King et al., *Cancer Res.* 54:6176–6185 (1994); and Wilbur et al., *Bioconjugate Chem.* 5:220–235 (1994), all of which are hereby expressly incorporated by reference). It should be understood that the candidate agents may be attached in a variety of ways, including those listed above. What is important is that manner of attachment does not significantly alter the functionality of the candidate agent; that is, the candidate agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01%–0.02% tween 20 (surfactant), and rinsed again with a pH 7.7 PBS plus 0.01% tween 20. Finally, the enzyme is added to the solution, preferably after being prefiltered using a 0.45 $\mu$m amicon micropure filter.

In a preferred embodiment, in addition to a bioactive agent, the microspheres comprise an optical signature that can be used to identify the attached bioactive agent. That is, each subpopulation of microspheres comprises a unique optical signature or optical tag that can be used to identify the unique bioactive agent of that subpopulation of microspheres; a bead comprising the unique optical signature may be distinguished from beads at other locations with different optical signatures. As is outlined herein, each bioactive agent will have an associated unique optical signature such that any microspheres comprising that bioactive agent will be identifiable on the basis of the signature. As is more fully outlined below, it is possible to reuse or duplicate optical signatures within an array, for example, when another level of identification is used, for example when beads of different sizes are used, or when the array is loaded sequentially with different batches of beads.

In a preferred embodiment, the optical signature is generally a mixture of nanocrystals. By "nanocrystal", "quantum dot" or "semiconductor cluster" herein is meant a particle less than 30 nm that displays luminescence. However, it is understood that a single nanocrystal can serve as an optical signature. By varying the material, size and concentration of the nanocrystal, matrices of unique tags may be generated. This may be done by attaching the nanocrystals to the surface of the beads, or alternatively, by embedding the nanocrystals within the bead, as is outlined below.

In a preferred embodiment, different concentrations of nanocrystals can be used as different codes. In a preferred embodiment, the encoding can be accomplished in a ratio of at least two different nanocrystals, wherein the nanocrystals can be different by size and/or material, although more encoding dimensions may be added such as in the size of the beads, for example. In addition, the labels are distinguishable from one another; thus two different labels may comprise different molecules (i.e. two different sizes or materials) or, alternatively, one label at two or more different concentrations or intensities. Thus, ratios of different concentrations can be done as well.

The ability of a particular nanocrystal mixture to encode for different chemical functionalities depends on the resolution of the ratiometric measurement. Conservatively, any nanocrystal pair should provide the ability to discriminate at least twenty different ratios. The number of unique combinations of two nanocrystals made with a particular nanocrystal set is shown in the following Table I.

TABLE I

| Number of nanocrystals in set | Combinations possible |
|---|---|
| 3 | 3 |
| 4 | 6 |
| 5 | 10 |
| 6 | 15 |

Thus, using six nanocrystals and twenty distinct ratios for each nanocrystal pair, 300 separate chemical functionalities may be encoded in a given population of microspheres. Combining more than two nanocrystals provides additional diversity in the encoding combinations. Furthermore, the concentration of the nanocrystals will contribute to their intensity; thus intensity is another way to increase the number of unique optical signatures. In addition, extra "bits" of the combination set may be used for error correction as is known in the art.

In another example, four nanocrystals differing in particle size at ten distinguisable intensity levels (i.e. different amounts of nanocrystals in each mixture) gives $10^4$ or 10,000 codes.

When combinations of nanocrystals are used, a preferred embodiment combines the sets such that the emission range of the target signal is empty; that is, rather than detect an increase in absorption at the particular wavelength of the target signal due to the presence of a coding signal, nanocrystals emitting at the target signal wavelength are not used. This allows more sensitive detection.

In nanocrystals, the absorbance onset and emission maximum shift to higher energy with decreasing size. The excitation tracks the absorbance, resulting in a tunable fluorophore that that can be excited efficiently at any wavelength shorter than the emission peak yet will emit with the same characteristic narrow, symmetric spectrum regardless of the excitation wavelength. Variation of the material used for the nanocrystal and variation of the size of the nanocrystal afford a spectral range of at least 400 nm to 2 $\mu$m in the peak emission, with typical emission widths of 20 to 30 nm at room temperature (full width at half maximum (FWHM)) in the visible region of the spectrum and large extinction coefficients in the visible and ultraviolet range (approximately $10^5$ $M^{-1}$ $cm^{-1}$). Narrower emission widths may be obtained at lower temperatures.

Metallic and magnetic nanocrystals, with the appropriate organic derivatization of the surface, have been previously described. See, e.g., Bruchez, supra, Chan and Nie, supra, Miltenyi, et al., Cytometry, 11:231 (1990); Lackle, Histochem. Cell Biol., 106:9 (1996); Hermann, et al., Histochem. Cell Biol., 106:31 (1996); Elghanlan, et al., Science, 277:1078 (1997); Alivisatos, et al., Nature, 382:609 (1996); Mirkin, et al., Nature, 382:607 (1996); and Beverloo, et al., Cytometry, 11:784 (1990). Preferred materials include CdSe, InP, InAs, GaAs and CdS.

Bandgap engineering concepts borrowed from materials science and electronics have led to the development of core-shell nanocrystals. By enclosing a core nanocrystal of one material with a shell of another having a larger bandgap, one can efficiently confine the excitation to the core, eliminating nonradiative relaxation pathways and preventing photochemical degradation. Thus, in a preferred embodiment, the nanocrystals comprise a core and a shell. For example, preferred embodiments include a CdSe core and a AnS or CdS shell. Other examples use CdS/HgS/CdS, InAs/GaAs, GaAs/AlGaAs and CdSe/ZnS.

Additionally, in the most preferred embodiment, the nanocrystals are coated for increased solubility of the crystals. Preferably, the coating is of silica. Moreover, the nanocrystals can comprise mercaptoacetic acid for solubilization and covalent protein attachment. When reacted with ZnS-capped CdSe nanocrystals in chloroform, the mercapto group binds to a Zn atom, and the polar carboxylic acid group renders the nanocrystal water soluble. The free carboxyl group is also available for covalent coupling to various biomolecules (such as proteins, peptides, and nucleic acids) by cross-linking to reactive amine groups. Reagents which produce similar results can also be use.

In a preferred embodiment, the nanocrystals are covalently attached to the surface of the beads. This may be done as is generally outlined for the attachment of the bioactive agents, using functional groups on the surface of the beads. As will be appreciated by those in the art, these attachments are done to minimize the effect on the nanocrystal.

In a preferred embodiment, the nanocrystals are non-covalently associated with the beads, generally by embedding the nanocrystals in the bead matrix or pores of the beads. This may be done during synthesis of the bead. By incorporating label molecules (including nanocrystals, collodial metals, nanometer size particles, etc), into stable porous materials and then encapsulating them, extremely stable optically active beads are made, for use in this invention as well as other systems. Generally, this aspect of the invention includes soaking the porous material, such as porous silica, in a solution of dye and monomer, and/or crosslinking agent, and then rinsing the beads of any free dye and monomer on the surface of the porous material. The residueal material left in the pores is then polymerized, creating a non-diffusable barrier or in some cases actually covalently immobilizing the dye within the pore. Since the encoding molecules, including nanocrystals, are encapsulated into the polymer, they will not come in direct contact with organic solutions, and will also be less likely to leach out during subsequent synthesis or assay. Moreover, since the encoding molecules are physically trapped inside the polymer immobilized in the solid phase's pores, the dyes are spatially separated from any dyes on the particle's surface (e.g. the target signal dyes), thus abrogating the change of flourescence energy transfer or resonance electron transfer. Furthermore, this reduces the possibility of physical interaction, including aggregation.

These encapsulated beads may be used not only in the present invention but also in diagnostic assays, labelling of organelles and other cellular biological applications, analytical methods including laser based flow cytometry, capillary electrophoresis, mass spectrometry and spectroscopy (UV/VIS, IR, Near IR, FTIR, etc.).

In addition, since this method does not rely on the use of reactive groups on the dye for attachment, dyes that are not easily derivatized with such reactive groups can be used.

A preferred method of encapsulation utilizes sol-gel polymerization; see Corriu et al., Angew. Chem. Int. Ed. Engl. 35:1420–1436 (1996), and cited references, hereby incorporated by reference in entirety.

In one embodiment, the nanocrystals are added to the bioactive agent, rather than the beads, although this is generally not preferred.

As an illustration of forming a bead, an aliquot of stock microspheres are vacuum filtered to produce a dry cake. In one implementation, microsphere copolymers of methylstyrene (87%) and divinylbenzene (13%) are used that have a 3.1 micrometer ($\mu$m) diameter. The dry cake is then broken apart and a nanocrystal solution added to it to encode optical signatures of the microspheres with information concerning the intended surface chemical functionalities. Nanocrystals may be covalently bonded to the microspheres' surface, or, the microspheres are placed in a nanocrystal solution preferably comprising a ratio of two or more nanocrystals dissolved in an organic solvent that will swell the microspheres, e.g., dimethylformamide (DMF). The length of time the microspheres are soaked in the nanocrystal solution will determine their intensity and the broadness of the ratio range.

It is understood that the nanocrystals can be used in conjunction with conventional fluorophores, such as organic dyes. Thus, an optical signature may comprise a nanocrystal on one bead (or target) and an organic dye on another bead (or target), or the optical signature may comprise both a nanocrystal and an organic dye on the same bead or target.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion- metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid—nucleic acid binding proteins pairs are also useful. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target; such a aptomer-target pair can be used as the IBL-DBL pair. Similarly, there is a wide body of literature relating to the development of binding pairs based on combinatorial chemistry methods.

In a preferred embodiment, the DBL may be attached to a bead, i.e. a "decoder bead", that may carry a label comprising at least one nanocrystal. As further outlined below, the IBL-DBL systems can be used in combination with other encoding or decoding systems. In each case, the assay or components utilize at least one nanocrystal. Therefore, the IBL-DBL binding pairs need not comprise a nanocrystal in each instance.

In one embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

In one embodiment, the IBL or the DBL comprises at least one nanocrystal, and its optical signature changes upon the binding the DBL. In one embodiment, the IBL and the DBL each comprise at least one nanocrystal, and the signal changes as a result of the interaction.

Alternatively, the IBL is a molecule whose color or luminescence properties change in the presence of various solvents. For example, the IBL may be a fluorescent molecule such as an ethidium salt whose fluorescence intensity increases in hydrophobic environments.

Similarly, the IBL may be a derivative of fluorescein whose color changes between aqueous and nonpolar solvents.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 base pairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

In a preferred embodiment, the microspheres do not contain an optical signature. That is, as outlined in U.S. Ser. Nos. 08/818,199 and 09/151,877, previous work had each subpopulation of microspheres comprising a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. Thus the previous work assigned each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

Thus, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use of optical signatures one some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants. However, as is more fully discussed below, the size of the array may be further increased if another parameter is included such as concentration or intensity; thus for example, if two different concentrations of the IBL are used, then the array size increases as $3^n$. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

Once the microspheres, which in some cases comprise candidate agents and unique tags, are generated, they are added to the substrate to form an array. In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads removed.

It should be noted that not all sites of an array may comprise a bead; that is, there may be some sites on the substrate surface which are empty. In addition, there may be some sites that contain more than one bead, although this is generally not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface.

In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags, and/or mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead comprises a nanocrystal. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached bioactive agent may be done directly, for example using mass spectroscopy.

Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs). As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled", herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent labels; although labels include enzymes and particles such as magnetic particles as well. Preferred labels include luminescent labels. In the most preferred embodiment, the label comprises at least one nanocrystal. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and either the IBL or the bioactive agent (i.e. a hybridization between the candidate probe and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used in an assay, during the assay, or after the assay.

In one embodiment, a single decoding step is done. In this embodiment, each DBL is labeled with a unique label, such that the number of unique tags is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1–16), and four unique tags (four different nanocrystals, for example; labels A–D). Decoder probes 1–16 are made that correspond to the probes on the beads. The first step is to label decoder probes 1–4 with tag A, decoder probes 5–8 with tag B, decoder probes 9–12 with tag C, and decoder probes 13–16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc. In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture comprising at least one nanocrystal. By varying both the composition of the mixture (i.e. the ratio of one nanocrystal to another), particle size and the concentration of the nanocrystal (leading to differences in signal intensity), matrices of unique optical signatures may be generated as described above.

In a preferred embodiment, a spatial or positional coding system is done. In this embodiment, there are sub-bundles or subarrays (i.e. portions of the total array) that are utilized. By analogy with the telephone system, each subarray is an "area code" that can have the same tags (i.e. telephone numbers) of other subarrays, but are separated by virtue of the location of the subarray. Thus, for example, the same unique tags can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same nanocrystal ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In any variety of the embodiments described above, the microsphere system may be attached to the distal end of the optical fiber bundle using a variety of compatible processes. The microspheres are located close to the end of the bundle. This ensures that the light returning in each optical fiber predominantly comes from only a single microsphere. This feature is necessary to enable the interrogation of the optical signature of individual microspheres to identify reactions involving the microsphere's functionality and also to decode the nanocrystal ratios contained in those microspheres. The adhesion or affixing technique, however, must not chemically insulate the microspheres from the analyte.

Preferably, each optical fiber of a bundle conveys light from a single microsphere contained in its well. Consequently, by imaging the end of a bundle onto a CCD array, the optical signatures of the microspheres are individually interrogatable.

As an example, to form the microwells and to place the microspheres in the wells, a 1 mm hexagonally-packed imaging fiber contains approximately 20,600 individual optical fibers that have cores approximately 3.7 $\mu$m across (Part No. ET26 from Galileo Fibers). Typically, the cores of each fiber are hexagonally shaped as a result the starting preform; that is, during drawing the fiber does not usually change shape. In some cases, the shape can be circular, however.

Further in this example, both the proximal and distal ends of the fiber bundle are successively polished on 12 $\mu$m, 9 $\mu$m, 3 $\mu$m, 1 $\mu$m, and 0.3 $\mu$m lapping films. Subsequently, the ends can be inspected for scratches on an atomic force microscope. A solution of 0.2 grams $NH_4F$ (ammonium fluoride) with 600 $\mu$l distilled $H_2O$ and 100 $\mu$l of HF (hydrofluoric acid), 50% stock solution, may be used. The distal end is etched in this solution for a specified time, preferably approximately 30 to 600 seconds, with about 80 seconds being preferred.

Upon removal from this solution, the bundle end is immediately placed in deionized water to stop any further etching. The fiber is then rinsed in running tap water. At this stage, sonication is preferably performed for several minutes to remove any salt products from the reaction. The fiber is then allowed to air dry.

The foregoing procedure produces wells by the anisotropic etching of the fiber cores favorably with respect to the cladding for each fiber of the bundle. The wells have approximately the diameter of the cores, 3.7 $\mu$m. This diameter is selected to be slightly larger than the diameters of the microspheres used, 3.1 $\mu$m, in the example. The preferential etching occurs because the pure silica of the cores etches faster in the presence of hydrofluoric acid than the claddings.

The microspheres are then placed in the wells according to a number of different techniques. The placement of the microspheres may be accomplished by dripping a solution containing the desired randomly mixed subpopulations of the microspheres over the distal end, sonicating the bundle to settle the microspheres in the wells, and allowing the microsphere solvent to evaporate. Alternatively, the subpopulations could be added serially to the bundle end. The microspheres may then be fixed into the wells by using a dilute solution of sulfonated Nafion that is dripped over the end. Upon solvent evaporation, a thin film of Nafion was formed over the microspheres which holds them in place. This approach is compatible for fixing microspheres for pH indication that carry FITC functionality. The resulting array of fixed microspheres retains its pH sensitivity due to the permeability of the sulfonated Nafion to hydrogen ions. This approach, however, cannot be employed generically as Nafion is impermeable to most water soluble species. A similar approach can be employed with different polymers. For example, solutions of polyethylene glycol, polyacrylamide, or polyhydroxymethyl methacrylate (polyHEMA) can be used in place of Nafion, providing the requisite permeability to aqueous species.

An alternative fixation approach employs microsphere swelling to entrap each microsphere in its corresponding microwell. In this approach, the microspheres are first distributed into the microwells by sonicating the microspheres suspended in a non-swelling solvent in the presence of the microwell array on the distal end. After placement into the microwells, the microspheres are subsequently exposed to an aqueous buffer in which they swell, thereby physically entrapping them, analogous to muffins rising in a muffin tin.

One of the most common microsphere formations is tentagel, a styrene-polyethylene glycol co-polymer. These microspheres are unswollen in nonpolar solvents such as hexane and swell approximately 20–40% in volume upon exposure to a more polar or aqueous media. This approach is extremely desirable since it does not significantly compromise the diffusional or permeability properties of the microspheres themselves.

In most environments, it may be unnecessary to use any.chemical or mechanical fixation for the microspheres. In a preferred embodiment, particularly when wells are used, a sonication step may be used to place beads in the wells.

Once made, the compositions of the invention find use in a number of applications. In a preferred embodiment, the compositions are used to probe a sample solution for the presence or absence of a target analyte, including the quantification of the amount of target analyte present. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, Salmonella, Campylobacter, *Vibrio cholerae*, Leishmania, enterotoxic strains of *E. coli*, and Legionnaire's disease bacteria. Similarly, bioremediation strategies may be evaluated using the compositions of the invention.

In a Further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33–39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "artificial noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$–$10^{-6}$ $M^{-1}$ with less than about $10^{-5}$ to $10^{-9}$ $M^{-1}$ being preferred and less than about $10^{-7}$–$10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in in optical signal. This change can occur via many different mechanisms. A few examples include the binding of a nanocrystal-tagged analyte to the bead, the production of a nanocrystal species on or near the beads, the destruction of an existing nanocrystal species, a change in the optical signature upon analyte interaction with nanocrystal on bead, or any other optically interrogatable event.

In a preferred embodiment, the change in optical signal occurs as a result of the binding of a target analyte that is labeled, either directly or indirectly, with a detectable label, preferably comprising at least one nanocrystal.

As an example provided herein, when a proteinaceous target analyte is used, it may be either directly labeled with at least one nanocrystal, or indirectly, for example through the use of a labeled antibody. Similarly, nucleic acids can be labeled with a nanocrystal, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalatois and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

In one embodiment, the bead does not comprise a luminescent label but the target does, therefore, the change is the detection of the optical signature of the target comprising at least one nanocrystal wherein the target is bound to the bead. For further descriptions of attaching nanocrystals to biomolecules, see for example, Bruchez supra and Chan and Nie supra.

In one example, the nanocrystal is attached to the microsphere, target, DBL, or bioactive agent through an avidin-biotin interaction. Biotin is covalently bound to the nanocrystal surface and the biotinylated nanocrystals are used to label the bead, target, etc., which have been incubated in phalloidin-biotin and streptavidin. Other classic ligand-receptor binding models as known in the art can be used to attach the nanocrystals to compositions as desired.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with a nanocrystal on the bead may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc., which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different nanocrystal, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is done using the compositions of the invention. In this embodiment, a DNA polymerase is used to extend a primer using fluorescently labeled ddNTPs. The 3' end of the primer is located adjacent to the SNP site. In this way, the single base extension is complementary to the sequence at the SNP site. By using four different nanocrystals, one for each base, the sequence of the SNP can be deduced by comparing the four base-specific signals. This may be done in several ways. In a first embodiment, the capture probe can be extended; in this approach, the probe must either be synthesized 5'–3' on the bead, or attached at the 5' end to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

In addition, when the target analyte and the DBL both bind to the agent, it is also possible to do detection of non-labelled target analytes via competition of decoding.

In an embodiment wherein the targets are directly or indirectly labeled, the label comprises at least one nanocrystal.

In a preferred embodiment, the methods of the invention are useful in array quality control. Prior to this invention, no methods have been described that provide a positive test of the performance of every probe on every array. Decoding of the array not only provides this test, it also does so by making use of the data generated during the decoding process itself. Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal-this can be detected during decoding. The omission of one or more agents from multiple arrays can also be detected. An advantage of this quality control procedure is that it can be implemented immediated prior to the assay itself, and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In a preferred embodiment, the arrays can be used to do reagent quality control. In many instances, biological macromolecules are used as reagents and must be quality controlled. For example, large sets of oligonucleotide probes may be provided as reagents. It is typically difficult to perform quality control on large numbers of different biological macromolecules. The approach described here can be used to do this by treating the reagents (formulated as the DBLs) as variable instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal so that the concentration of the target analyte can be estimated. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array. Thus, in this embodiment, the sequential decoding scheme is implemented with different concentrations being used as the code "labels", rather than different nanocrystals. In this way, signal as a response to concentration can be measured for each bead. This calibration can be carried out just prior to array use, so that every probe on every array is individually calibrated as needed.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development.

Similarly, in a preferred embodiment, the methods of the invention are useful in quantitation in assay development. A major challenge of many assays is the ability to detect differences in analyte concentrations between samples, to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996), hereby incorporated by reference in its entirety. While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, this can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are chosen empirically, which avoids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

All references cited herein are incorporated by reference in their entirety.

We claim:

1. A composition comprising:
   a) a substrate with a surface comprising discrete sites, wherein said discrete sites are wells; and
   b) a population of microspheres randomly distributed on said discrete sites, wherein at least one of said microspheres comprises a nanocrystal.

2. A composition according to claim 1 wherein said nanocrystal is embedded in said microsphere.

3. A composition according to claim 1 wherein said nanocrystal is sealed into porous silica using a sol-gel polymerization process.

4. A composition according to claim 1 wherein said nanocrystal is attached to said microsphere.

5. A composition according to claim 1 wherein said microsphere comprising said nanocrystal further comprises at least one additional nanocrystal.

6. A composition according to claim 1 wherein at least a plurality of said microspheres comprises a nanocrystal.

7. A composition according to claim 1 wherein at least two microspheres comprise an optical signature which differ from one another.

8. A composition according to claim 1 wherein said microspheres comprise bioactive agents.

9. A composition according to claim 8 wherein said bioactive agents comprise nucleic acids.

10. A composition according to claim 8 wherein said bioactive agents comprise proteins.

11. A composition according to claim 10 wherein said proteins are selected from the group consisting of enzymes and antibodies.

12. A composition according to claim 1 wherein said population of microspheres comprises at least a first and a second subpopulation comprising:
   i) a first and a second bioactive agent, respectively; and
   ii) a first and a second optical signature, respectively, capable of identifying each bioactive agent, wherein at least one of said optical signatures comprises said nanocrystal.

13. A composition according to claim 12 wherein at least one of said optical signatures comprises at least two nanocrystals.

14. An array composition comprising:
   a) a substrate with a surface comprising discrete sites, wherein said discrete sites are wells; and
   b) a population of microspheres comprising at least a first and a second subpopulation, wherein each subpopulation comprises a bioactive agent bound to a target analyte comprising a nanocrystal, wherein said microspheres are randomly distributed on said surface.

15. An array composition comprising:
   a) a substrate with a surface comprising discrete sites, wherein said discrete sites are wells; and
   b) a population of microspheres comprising at least a first and a second subpopulation, wherein each subpopulation comprises:
      i) a bioactive agent; and
      ii) an identifier binding ligand bound to a decoder binding ligand comprising a nanocrystal such that the identification of the bioactive agent can be elucidated;
   wherein said microspheres are randomly distributed on said surface.

16. A composition according to claim 14 or 15 wherein said bioactive agents are nucleic acids.

17. A composition according to claim 14 or 15 wherein said bioactive agents are proteins.

18. An array composition comprising:
   a) a substrate with a surface comprising discrete sites, wherein said discrete sites are wells; and
   b) a population of microspheres comprising at least a first and a second subpopulation, wherein each subpopulation comprises a bioactive agent bound to a decoder binding ligand comprising a nanocrystal, wherein said microspheres are randomly distributed on said surface.

* * * * *